United States Patent [19]

Ishii

[11] 4,152,410

[45] May 1, 1979

[54] DIAGNOSIS REAGENT FOR NEOPLASM AND METHOD FOR DIAGNOSIS OF NEOPLASM

[75] Inventor: Masaru Ishii, Urawa, Japan

[73] Assignee: Eisai Co., Ltd., Tokyo, Japan

[21] Appl. No.: 719,505

[22] Filed: Sep. 1, 1976

[30] Foreign Application Priority Data

| Sep. 3, 1975 | [JP] | Japan | 50-105882 |
| Sep. 3, 1975 | [JP] | Japan | 50-105883 |
| Sep. 4, 1975 | [JP] | Japan | 50-106483 |
| Sep. 4, 1975 | [JP] | Japan | 50-106484 |
| Sep. 4, 1975 | [JP] | Japan | 50-106485 |
| Sep. 4, 1975 | [JP] | Japan | 50-107228 |
| Jun. 8, 1976 | [JP] | Japan | 51-66071 |

[51] Int. Cl.$^2$ .............................................. A61K 43/00
[52] U.S. Cl. ...................................... 424/1; 23/230 B; 424/12; 424/85; 424/88
[58] Field of Search .................... 23/230 B; 424/1, 12, 424/85, 88

[56] References Cited

U.S. PATENT DOCUMENTS

| 3,663,684 | 5/1972 | Freedman et al. | 424/1 |
| 3,697,638 | 10/1972 | Hansen | 424/1 |
| 3,852,415 | 12/1974 | Vandervoorde | 424/1 |
| 3,867,363 | 2/1975 | Hansen | 424/1 X |
| 3,927,193 | 12/1975 | Hansen et al. | 424/1 |
| 3,960,827 | 6/1976 | Bjorklund | 23/230 B |

*Primary Examiner*—Leland A. Sebastian
*Attorney, Agent, or Firm*—Wenderoth, Lind & Ponack

[57] ABSTRACT

NEA (Neoplasm embryonic antigen) and NEA antibody; diagnosis reagents for neoplasm comprising a substance selected from the group consisting of NEA antibody, NEA or NEA antibody labelled with a radioactive isotope, a combined product of NEA or NEA antibody with a particulate substance, a gel plate containing NEA antibody, and a carbamylated NEA antibody; methods for the diagnosis of neoplasm; processes for the production of NEA antibody; and methods for the purification of NEA and NEA antibody. The reagents are very useful for the diagnosis of neoplasms.

29 Claims, No Drawings

DIAGNOSIS REAGENT FOR NEOPLASM AND METHOD FOR DIAGNOSIS OF NEOPLASM

This invention relates to a new diagnosis reagent for neoplasm, and method for the diagnosis of neoplasm.

Study of the inherent antigenic substance (hereinafter referred to as antigen) in human neoplasm is an important factor in considering the causal genesis, the prevention, the treatment, and the diagnosis of the neoplasm.

Recently, several attempts have been made to find an antigen associated with neoplasm, resulting in the certain antigens have been reported. They are, for example, α-feto-protein for primary cancer of liver cells, and Carcino Embronic Antigen (CEA) for adenocarcinoma, or the like. These antigens are however restricted to neoplasms of some particular viscera or diseased tissue. For this reason, substantial progress would be made in the diagnosis of neoplasm, and the prevention and treatment of various human neoplasms, by researching antigens which are common to the neoplasms of various viscera and diseased tissue, preparing monospecific antibodies for said antigens, and establishing a method for the detection of an antigen using a monospecific antibody.

We have found a novel neoplasm embryonic antigen (hereinafter referred to as NEA), as a result of research on the existence of an antigen which is common to a wide range of various neoplasms.

"NEA" according to this invention is an abbreviation of neoplasm embryonic antigen, a term coined by the present inventor.

NEA is an antigen common to both the fetus and neoplasms. The said antigen can be obtained from a cancerous tissue such as for example cancers of the breast, the stomach, the liver, and the like.

The present invention has been completed on the basis of the fact that the NEA or the NEA antibody can be used for diagnosis of various kinds of malignant neoplasm.

An object of this invention is therefore to provide a new diagnosis reagent for a wide range of neoplasms, which can be practically used.

Another object of this invention is to provide a method for the diagnosis of human neoplasm.

Another object of this invention is to provide a process for the production of NEA antibody for diagnosis of neoplasm.

Further object of this invention is to provide a method for the purification of the NEA and the NEA antibody to be used as diagnosis reagent for neoplasm.

NEA has the following properties.

(1) It can be proved by the Ouchterlony method using an antibody for the NEA that NEA exists in tissue (mainly small intenstine and large intestine), serum, ascites and excrement of an embryo, as well as in tissue of various neoplasms (mainly malignant neoplasms), and in serum and ascites of patients with neoplasm. However, the existence of the NEA in non-neoplastic tissue of patients with neoplasm, in serum of a normal human, and in serum and ascites of a non-neoplasm patient, cannot be proved.

Moreover, there cannot be shown de-activation or diminution of activity of the NEA antibody, even if anti-NEA serum is subjected to neutralization and absorption, using antigen extracted from the tissue of a non-neoplasm patient, serum of a normal human, and serum of a non-neoplasm patient. However, by the Ouchterlony method, the de-activation or diminution of activity of the NEA antibody can be proved when the antiserum is subjected to absorption using an extract from embryo tissue, embryo serum, an extract from some malignant neoplasm tissue or serum of a neoplasm patient.

It is therefore concluded that NEA is a fetal antigen which is also common to neoplasms.

(2) It is proved by the Ouchterlony method and immunoelectrophoresis that NEA is brought into the γ-globulin region by immunoelectrophoresis using a barbital solution containing a cellulose acetate membrane, Pevicon C-870 (vinyl chloride-vinyl acetate complex), agar gel, starch or the like as a supporting medium, the barbital solution having a pH of 8.6 and an ionic strength of 0.025–0.1, and the NEA differs from the known immuno-globulins (immuno globulin G, A, M, D and E) and other serum γ-globulin in terms of immunology.

(3) Photo-absorption coefficient of the NEA is $E_1\ cm^{0.1\%}\ 280 = 0.936$. The amount of the protein was measured by the Lowry method wherein bovine albumin is selected as the standard base.

(4) It is shown as a result of determination of molecular weight by column chromatography using Sephadex G-200 (Trade Mark, Pharmacia AB) that NEA is a protein having a molecular weight of $100,000 \pm 20,000$.

(5) The NEA has such property that when the NEA is developed by a buffer solution having an ionic strength of 0.05 and pH of 7.0 by means of chromatography using a basic anion exchanger, the NEA is not adsorbed on the exchanger, but is eluted with immuno globulin G.

(6) Isoelectric point of the NEA shows pH 9.1–9.4.

(7) The NEA precipitates in 2.6 M ammonium sulfate solution at pH 7.0.

As stated above, the NEA is a fetal antigen common to neoplasms. Diagnosis of the neoplasm can therefore be effected by detecting the existence of the NEA in the serum.

The NEA antibody for diagnosis of neoplasm according to this invention can be produced by using the NEA alone or the NEA-NEA antibody complex to immunize animals other than humans, and recovering an antiserum.

The NEA in this invention can be used either in a crude form or in a purified form, for example, embryo serum, embryo ascite, serum of a neoplasm patient, ascite of a neoplasm patient, extract of tissue extirpated from a neoplasm, and extract of embryo excrement, as well as refined products thereof which are obtained by a method for purifying a protein fraction.

Purification can be accomplished by any conventional methods in the immunological field for purifying a protein fraction. The said methods include, for example, a method of salting out, electrophoresis, gel filtration, ion exchange, affinity chromatography, centrifugal separation, ultra-filtration, isoelectric point fractionation, organic solvent fractionation, Cohn's fractionation and modified Spiro method, a method which comprises adding NEA antibody to the crude NEA, collecting the NEA-NEA antibody complex, and isolating the NEA therefrom, and a method which comprises adding an antibody against impurities, except for the NEA, to remove the impurities. These methods may be usually employed in any combination form.

The NEA-NEA antibody complex can be obtained, for example, by mixing NEA with NEA antibody in a solution.

As for these methods for the purification, there may be mainly employed (A) a method using affinity chromatography and (B) a method comprising treatment with a basic anion exchange resin. These methods are explained in detail as follows:

(A) Method using affinity chromatography

The NEA or the NEA antibody is combined with a supporting medium such as Sepharose (Trade Mark, Pharmacia AB), Sephadex (Trade Mark, Pharmacia AB), and the like. More particularly, a supporting medium which was previously activated with cyan bromide or the like, is added to a solution of the NEA or the NEA antibody, and the mixture is stirred at a low temperature. The resulting product is used as an agent for carrying out purification. A combined product of the NEA antibody and a supporting medium is used for the purification of the NEA, while a combined product of the NEA and a supporting medium is used for the purification of the NEA antibody. In practice, a column is filled with the combined product of the NEA and supporting medium. Alternatively, the column is filled with a combined product of the NEA antibody and supporting medium. A solution containing the NEA or the NEA antibody to be purified is charged in the column. By such a step, only the NEA or the NEA antibody is reacted with the NEA antibody or the NEA which is combined with the supporting medium, to form a complex, and the other impurities flow out of the column. The complex is then dissociated to obtain the objective NEA or the NEA antibody. Such dissociation of the complex can be achieved by introducing a 3-5 M salt solution or an aqueous solution of pH 2-3 into the column.

According to this purification method the NEA or the NEA antibody can be obtained in high purity, not only from a starting material rich in NEA or NEA antibody, but also from a starting material containing a small amount of NEA or NEA antibody. Further, there is an advantage that the column used in this method can be repeatedly used after regeneration.

(B) Purification of the NEA with basic anion exchange resin

There can be used, as basic anion exchange resins, QAE-Sephadex (Trade Mark, Pharmacia AB), DEAE-Sephadex (Trade Mark, Pharmacia AB), DEAE-Cellulose (Serva Co.), TEAE-Cellulose (Serva Co.), and the like, for example.

As an NEA-containing composition, there can be used any composition containing NEA, exemplified by embryonic serum, serum of neoplasm patient, ascites of neoplasm patient, extract of tissue extirpated from a neoplasm, extract of excrement of an embryo, as well as a partially purified NEA which is obtained by a method for the purification of protein fraction of the above materials.

Basic anion exchange resin is filled in a column, and the above NEA-containing composition is then introduced into the column. By such a step, the NEA can be purified, because the NEA is eluted without absorbing onto the resin. Batch system can be used for the purification, in place of the above column system.

The NEA antibody can be obtained by immunizing animals with the purified NEA according to the method of this invention.

As indicated above, NEA antibody is obtained by immunizing animals other than humans with the NEA or the NEA-NEA antibody complex, and collecting the blood serum of the animals after a certain predetermined period of time. Animals to be used for this purpose include rabbits, goats, horses, cows and the like. When immunization is effected, it is preferable to immunize with the NEA or the NEA-NEA antibody complex which has previously been emulsified by using Freund complete adjuvant, and to immunize not only once, but several times, so that antiserum having high antibody value may be obtained.

There can be used several means for removing antibodies other than the NEA antibody contained in the resulting anti-serum. Such means are exemplified as follows:

An immuno-adsorption method wherein the antigen is selected from the serum of a normal human, the ascites and the serum of a non-neoplasm patient, or the extract of neoplastic tissue;

An affinity chromatography wherein said antigen is fixed on a supporting medium;

An affinity chromatography wherein the NEA is fixed on a supporting medium;

A method which comprises adding the NEA to the anti-serum to isolate the NEA-NEA antibody complex, and separating the NEA antibody from the complex; and the like.

According to this invention, diagnosis for neoplasm can be carried out by usually employing NEA antibody through an application of an antigen-antibody reaction. That is to say, diagnosis is effected by means of an application of the reaction of NEA antibody with NEA in the samples. Further, diagnosis for neoplasm can also be carried out by employing NEA per se, through an inhibitory reaction using NEA antibody.

For diagnosis of neoplasm (detection of the NEA) using the NEA antibody obtained by this invention, the following methods may be used for example:

(1) Ouchterlony method, and the corresponding modified Cohn method.
(2) Single radial immunodiffusion method (S. R. I. D.)
(3) Electrophoresis method (Counter electrophoresis, immunoelectro-osmophoresis, immunoelectrodiffusion)

When this method is used, both the NEA antibody and the antigen in the test serum tend to easily move toward the γ-globulin region, and accordingly, one of them must be carbamylated so as to easily move toward the albumin region. In spite of said carbamylation, both the NEA antibody and the antigen in the test serum are not de-activated in their immuno activities as the antibody or antigen.

(4) Radioimmuno assay (RIA)
(5) Enzyme immuno assay (ELISA)
(6) Bacteriophage method
(7) Complement fixation method (CF)
(8) Hemagglutination method (PHA, RPHA)
(9) Immune adherence hemagglutination (IA)

Any of these methods may be used.

The following is a detailed explanation of a process for diagnosing neoplasm by immunoelectro-osmophoresis as classified above in item 3.

Immunoelectro-osmophoresis is based on the principal that an agar-plate is provided with a pair of wells therein; anti-serum is injected into the well on the anode side, while antigen (test serum) is injected into the well on the cathode side; an electric current is transmitted for a certain period of time; the antigen is subjected to phoresis to the anode; and the antibody moves to the cathode, resulting in a precipitation reaction in the gel at the area where the antigen and the antibody meet each other, to form a precipitation line. Refer to Biochim. Biophys. Acta, 34:258, 1959. This method has an advantage that the result is concluded within a considerably short period of time, and is superior in that it has relatively good sensitivity. In order to detect the antigen or the antibody, however, it is necessary that the antigen and the antibody move in reverse directions of each other. Since the NEA moves in the cathode direction, which is the same direction as the NEA antibody moves, the NEA cannot be detected by means of the conventional method as mentioned above. In order to detect the NEA antigen according to this method, therefore, the NEA or the NEA antibody has to be changed, so that its movement during electrophoresis is toward the anode side, provided that the respective inherent activities of the NEA and the NEA antibody are maintained.

According to this invention, the NEA antibody is carbamylated, so that it easily moves to the anode side. In order to detect the antigen in the test serum, it is apparent that the use of the carbamylated antibody is convenient and practical, as compared with the carbamylation of the antigen. Carbamylation of the NEA antibody can be carried out by mixing the NEA antibody in an aqueous potassium cyanate solution, incubating the mixture for a certain period of time, and finally cooling the same.

The carbamylated NEA antibody according to this method retains the original antibody activity of the NEA antibody, even after 4 months at 4° C.

Thus, the detection of the NEA in the serum of the patient, that is, the diagnosis of the neoplasm, can be carried out according to the immunoelectro-osmorphoresis method wherein the carbamylated NEA antibody according to this method is used.

Further, the following is a detailed explanation of a process for diagnosing neoplasm by the hemagglutination method (PHA method, or RPHA method) as classified above in item 8.

According to this method, the NEA or the NEA antibody is combined with fine particles which are conventionally used in the PHA method and RPHA method. It is particularly preferable to use blood cells of mammals and birds as the fine particles. There can also be used particles having a diameter of about 1-10μ, such as polystyrene latex, polyester latex, vinyl chloride, bentonite, glass beads, and the like.

Any conventional reagents can be used in order to combine the NEA or the NEA antibody with the fine particles. There may be enumerated glutaraldehyde, formaldehyde, tannic acid, bis-diazotized benzidine, chromium chloride, carbodiimide, and the like.

The following is an explanation of the general process for the production of the reagent according to this process wherein erythrocytes of sheep are used as starting material.

Erythrocytes of sheep are suspended in a phosphate physiological saline buffer solution, so as to result in a concentration of about 5%.

To the suspension, there is added one fifth (1/5) by volume of a glutaraldehyde solution, which was previously prepared by dissolving glutaraldehyde in the phosphate physiological saline buffer solution to a concentration of 1-5%, and the whole is stirred at room temperature for 3-7 hours. After the resulting product is washed with a physiological saline solution, a fresh phosphate physiological saline buffer solution is added, to produce 5% glutaraldehyde-erythrocytes of sheep. To the erythrocytes is added an equivalent amount of 0.001-0.02% tannic acid solution. After the mixture is stirred for 5-20 minutes, it was washed with physiological saline solution. To the resulting product, there is added phosphate physiological saline buffer solution, to produce 5% glutaraldehyde-tannic acid treated erythrocytes of sheep. In order to combine the thus treated erythrocytes with the NEA antibody, there are added to the erythrocytes 5 μg-1 mg/ml of the purified NEA antibody, which amount is equivalent to the amount of the erythrocytes, and the whole is stirred at room temperature for 10-60 minutes.

In order to combine the erythrocytes with the NEA, there is added to the erythrocytes 1 μg-1 mg/ml of the purified NEA, which amount is equivalent to the amount of the erythrocytes, and the whole is stirred at room temperature for 10-60 minutes.

The following is illustrative of the method for the detection of the NEA in the serum, by using the fine particles combined with the NEA or the NEA antibody according to this invention.

When the NEA antibody-fine particle product and the test serum are mixed with each other in a test tube, the NEA reacts with the NEA antibody to cause agglutination, if the NEA exists in the serum. As the result, sediment can be macroscopically recognized in the bottom of the tube, which is different from the usual or spontaneous sedimentation. When the serum does not contain the NEA or when the concentration of the NEA is less than the sensitivity of the present reagent, the NEA antibody-fine particle product is spontaneously precipitated, and a small spot is observed on the bottom of the tube. In the case of the NEA-fine particle product, there occurs the same agglutination as mentioned above, in the presence of the NEA antibody. In the latter case, agglutination is prevented in the presence of free NEA. Therefore, the free NEA in the serum is detected, by previously adding a suitable amount of the NEA antibody to the test serum, and adding the NEA-fine particles thereto, so as to observe whether or not agglutination occurs.

As the result of diagnosis of neoplasm in patients by the Ouchterlony method among the foregoing methods using the NEA antibody, it was shown that 27 of 84 cases were positive, concerning the serum of patients suffering from cancer of the stomach, the colon, the rectum, the pancreas, primary cancer of the liver, the uterus, the ovary, and the breast, leukemia and lymphosarcoma. On the contrary, 111 cases were all negative concerning the serum of normal humans and non-neoplasm patients. Further, as the result of the diagnosis by the single radial immunodiffusion method (S. R. I. D.), 38 of 98 cases were positive concerning the serum of neoplasm patients, while 140 of 141 cases were negative concerning the serum of normal humans and non-neoplasm patients. The NEA antibody according to this invention can therefore be used in monospecific diagnosis of neoplasms in general, especially malignant neoplasm.

Since the Ouchterlony method and single radial immunodiffusion method (S. R. I. D.) have relatively low sensitivity, it is considered that the efficiency of diagnosis can be improved by using a more sensitive method.

For the single radial immunodiffusion method (S. R. I. D.) as classified above in item (2) and the electrophoresis method as classified above in item (3), the following illustrates a diagnosis reagent for neoplasm which is used to detect the NEA and to diagnose the neoplasm, by means of immunoelectrodiffusion (Rauler method).

According to these methods, the NEA antibody is dissolved together with a supporting medium, and the solution is solidified to form a plate-like material.

As a supporting medium, there can be used any supporting medium which is conventionally employed in single radial immuno-diffusion method. Such supporting mediums include agar-agar, agarose, starch, polyacryamide gel, and the like, for example.

Any conventional method may be used for preparing a gel plate from the supporting medium and the NEA antibody. For instance, a supporting medium is dissolved under heat in a buffer solution, the NEA antibody is added thereto, and the whole is mixed. The resulting solution is placed on a glass plate or in a plastic vessel or pan, cooled, and solidified to obtain the desired plate.

In diagnosis using the gel plate obtained according to this method, a well is made in the gel plate, and the serum of the patient is injected into the well.

According to single radial immunodiffusion method, the plate is allowed to stand for a certain period of time, and thereafter, an observation is made as to whether or not a precipitation ring is formed.

According to immunoelectrodiffusion, an electric current is transmitted to the gel plate wherein the serum was previously injected, and an observation is made as to whether or not a precipitation band is formed.

When the precipitation ring or band is formed, it is proved that the NEA exists in the serum, thereby diagnosing the neoplasm in the patient.

The following is a detailed explanation of the reagent which can be used for detecting the NEA and diagnosing the neoplasm according to radioimmuno assay (RIA) as classified above in item 4.

The reagent of this method is produced by labelling a radioactive isotope on the NEA or the NEA antibody. Labelling can be carried out by any conventional technique. Such labelling can be effected, for example, by Chloramine T method or peroxidase method using $^{125}I$, $^{131}I$, and the like.

In order to estimate the NEA using the reagent of this method, there can be used any conventional method, such as double antibody method, solid phase method, and the like.

The NEA cannot be detected according to the Ouchterlony method in the serums of normal humans and non-neoplasm patients, whereas the NEA can be estimated according to the RIA method in the same serums. The concentration of NEA in these serums is relatively lower than that in the serum of the neoplasm patient, and diagnosis of the neoplasm can therefore be effected by using the concentration of the NEA in the serum of normal humans and non-neoplasm patients as the standard.

The above is a detailed explanation of this invention. The following is a summary of this invention.

A. A reagent comprising NEA or NEA antibody can be used for diagnosis of a wide range of neoplasms.

B. Diagnosis can be effected with a small amount of serum from the patient.

C. It is possible to screen for a neoplasm, and also to observe the progress of the neoplasm.

Following examples will serve to illustrate the invention, but should not be construed as limiting the invention thereto.

EXAMPLE 1

Partial purification of the NEA from the tissue of cancer 100 g of frozen tissue extirpated from the cancer of the breast were cut into small cubes. Physiological saline solution of 10 times by volume of the tissue was added thereto in a homogenizer. The mixture was then homogenized at the temperature of 4° C. for 10 minutes. Further, equivalent amount of physiological saline solution containing 0.05% of sodium nitride was added thereto. The mixture was stirred at 4° C. for 48 hours, and protein was extracted therefrom, which was in turn separated by centrifugation of 5000 gravitation (G) for 30 minutes. After removing the topmost fat layer, the supernatant liquid was collected. The resulting supernatant was again centrifuged at 2000 gravitation (G) for 30 minutes. The remaining small amount of the topmost fat layer was removed, and the supernatant was collected. Said supernatant was charged into a tube made of cellulose for dialysis, and concentrated to about 1/20 volume in the solution of polyethylene glycol (mean molecular weight is about 15,000). The concentrated supernatent showed the protein concentration of 73 mg/ml as the result of measurement by Lowry Folim method. 3 Ml of this concentrated solution were subjected to gel filtration in a buffer solution of barbital having pH of 8.6 and ionic strength of 0.05 by a column of 2.6 cm in diameter and 70 cm in length (bed capacity is 460 ml) which was previously filled with Sephadex G-200, and the eluate was fractionized.

When the elution was carried out, four peaks were shown at the wave length of 280 mµ by a spectrophotometer. More particularly, the four peaks consist of the first peak which is a fraction containing proteins of more than 19S and comprising $\alpha_2$-macroglobulin, immuno globulin M, $\beta$-lipoprotein and the like; the second peak which is a fraction of 7S globulin including immuno globulin; the third peak which is a fraction of 4.5S including albumin; and the fourth peak which is a fraction comprising materials of smaller molecular weights.

The NEA was eluted at an intermediate section between the second fraction and the third fraction. That is, about 90% of the NEA was eluted at a fraction of the molecular weight of 120,000–80,000. The eluate between the second peak and the third peak was collected, excluding those at the second peak and the third peak, resulting in a crude NEA fraction. The foregoing procedures were repeated, and the crude NEA fractions were concentrated to about 1/10 by volume on the basis of the original amount of the tissue, using a membrane for ultrafiltration (filterable molecular weight is less than 10,000). An electrophoresis chamber of 33 cm in length, 8 cm in width and 2 cm in thickness was filled with Pevicon C-870 as supporting medium. Using the barbital buffer solution having pH of 8.6 and ionic strength of 0.05, 5 ml of the concentrated solution of crude NEA fraction were injected in a slit which was placed at 10 cm away from the cathode side of said electrophoresis chamber, and subjected to the electrophoresis at 80 mA constant electric current for 16 hours. Since the NEA is 3-7 cm away from the slit toward the cathode side, the supporting medium at this area was cut off, and 100 ml of buffer solution comprising 0.05 M phosphate physiological saline solution at pH 7.5 were added thereto, and the whole was stirred. The supernatant was then collected by centrifugation at 3000 r.p.m. for 15 minutes. After adding another 100 ml of the same buffer solution to the supernatant with stirring, the supernatant was likewise collected by centrifugation under the same conditions. In order to remove the Pevicon C-870 which is slightly contaminated in said collected solution as an impurity, the collected solution was filtered by glass filter. About 200 ml of the filtrate were concentrated to 5 ml, by means of a Protein bag (Carl Schleicher G.m.b.H; Ultrahülsen No. 100, filterable molecular weight 25,000). The same operation as described above was repeated five times, and the resulting concentrated solution was maintained at 4° C. The electromobility of the resulting NEA was almost the same as that of the immuno globulin G. In this preparation or specimen, there are found immuno globulins G and A as contaminant protein by the Ouchterlony test and the immunoelectrophoresis.

According to the foregoing process, about 50% of the NEA could be recovered, calculating on the basis of the amount of the NEA in the first extract by physiological saline solution and purification degree amounted to about 100 times.

EXAMPLE 2

Partial purification of the NEA from the ascites of patient suffering from cancer Using an ultrafiltration membrane (filterable molecular weight is 15,000), 2 liters of the ascites of patient suffering from cancer of the stomach were concentrated to 500 ml. This concentrated solution was centrifuged for 30 minutes at 20,000 gravity (G) and the supernatant was collected. To the supernatant, 0.05 M phosphate physiological saline buffer solution at pH of 7.5 was added, until the total volume reached one liter (an amount of protein was about 3%). Ammonium sulphate was added to the mixture, so that 1.5 M ammonium sulphate solution was obtained. The solution was adjusted to pH 7.0 by adding sodium hydroxide. After this solution was allowed to stand for 60 minutes, the solution was centrifuged at 10,000 r.p.m. for 30 minutes. The supernatant was collected, and more ammonium sulphate was added thereto, so as to obtain 2.6 mol ammonium sulphate solution. After 60 minutes, the solution was centrifuged for 30 minutes at 10,000 r.p.m. More than 60% of the NEA was collected in the precipitate. The precipitate was dissolved in the barbital buffer solution having pH of 8.6 and ionic strength of 0.05, so as to make the total volume 200 ml.

This solution was subjected to gel-filtration by Sephadex G-50 (T.M., Pharmacia AB), using the same buffer solution as described above. The initially eluted protein fraction was collected, and was adjusted to about 70 mg/ml of protein concentration, and 5 ml of the solution were subjected to the electrophoresis. The procedure of the electrophoresis was as follows:

Pevicon C-870 (TM) as supporting medium was filled in an electrophoresis chamber of 33 cm in length, 8 cm in width and 2 cm in thickness. Using barbital buffer solution having pH 8.6 and ionic strength of 0.05, 5 ml of said fractional solution were injected into a slit which was provided at the portion 10 cm away from the cathode side in the chamber and the electrophoresis was effected at the constant electric current of 80 mA for 16 hours. The supporting medium in the area 3-7 cm away from the slit toward the cathode side was then cut off. 100 ml of 0.05 M phosphate physiological saline buffer solution of pH 7.5 were added with stirring, and the mixture was centrifuged at 3,000 r.p.m. for 15 minutes, to collect the supernatant. To the supernatant, there were added 100 ml of the same buffer solution as described above, and the mixture was stirred, and centrifuged under the same condition, and the resulting supernatant was filtered by a glass filter. The filtrate was concentrated to 2.5 ml by the protein bag. 2.5 ml of the concentrated solution were subjected to the gel-filtration through the column of 2.6 cm in diameter and 90 cm in length (bed capacity is 460 ml) wherein Sephadex G-200 was previously filled. By using 0.05 M phosphate buffer solution of pH 7.5, the eluate was collected and fractionized into each test tube. When the elution was effected, two absorption peaks were observed at the wave length of 280m$\mu$ by a spectrophotometer. The first peak corresponded to 19S fraction including immuno globulin M, while the second peak corresponded to 7S fraction including immuno globulin G. The NEA was eluted a little after the second peak. That is, about 90% of the NEA or above existed in the fraction corresponding to molecular weight of 120,000-80,000. This fraction was collected, and concentrated by the protein bag, followed by maintaining it at 4° C. In the resulting NEA preparation or specimen, there were observed the immuno globulins G and A as impurities by the Ouchterlony method and immunoelectrophoresis method. Purification degree of the resulting NEA amounted to about 50 times.

EXAMPLE 3

Production of the NEA antibody

Partially purified NEA according to Example 1 was processed to have an amount of protein of 1 mg/ml with physiological saline solution. To 0.5 ml of this solution, equivalent amount of Freund complete adjuvant was admixed, and the mixture was emulsified. The emulsion was divisionally subjected to an intracutaneous injection, a subcutaneous injection, and an intramuscular injection in the hind leg and the belly of a rabbit having the weight of about 2 Kg. After two weeks, an additional immunization was effected by using 1 ml of the NEA emulsion which was prepared as above. After the subsequent two weeks, further immunization was effected by using 1 ml of the same NEA emulsion. The blood was collected 10 days from the last immunization. The serum was separated from the blood, and the same was incubated at 56° C. for 30 minutes to bring it to a static state. For the purpose of antisepsis, sodium azide was then added to the serum, so that its concentration amounted to 0.05%. To this antiserum, there were added one third ($\frac{1}{3}$) by volume of serum of normal human and 5 mg of purified $\gamma$-globulin from colostrum per ml of the antiserum. The mixture was incubated at 37° C. for one hour, and then at 4° C. for 48 hours. Subsequently, it was centrifuged at 3,000 r.p.m. for 30 minutes at 4° C. to collect the supernatant. As the result of identification by Ouchterlony method and the immunoelectrophoresis method, using the extract of tissue of the original cancer of the breast as antigen, it was shown that the above-treated antiserum contained no antibody except for the NEA antibody. The purified $\gamma$-globulin from the colostrum is used for neutralization of antiserum for the reason that, since the tissue provided for extraction of antigen is the tissue of cancer of the breast, there is a possibility that the secretion type antigen of the immuno globulin A is contained in the preparation or specimen of the partially purified NEA; and since it is probable that the antibody for said antigen is formed in the antiserum thus prepared, there is used the purified γ-globulin from the colostrum which contains the immuno globulin A of secretion type antigen, for absorbing and removing the antibody.

EXAMPLE 4

Production of the NEA antibody

The partially purified NEA according to Example 2 was adjusted by physiological saline solution, so that the protein content amounted to 1 mg/ml. To 0.5 ml of said solution, equivalent amount of Freund complete adjuvant was added and mixed, and the mixture was emulsified. This emulsion was divisionally subjected to an intracutaneous injection, a subcutaneous injection, and an intramuscular injection in the hind leg and the belly of a rabbit having a weight of 2 Kg. After two weeks, an additional immunization was effected by using 1 ml of the NEA emulsion which was prepared by the same procedure as above-described. After the subsequent two weeks, further additional immunization was effected by using 1 ml of the same NEA emulsion. The blood was collected 10 days from the last immunization. The serum was separated from the blood. The resulting serum was incubated at 56° C. for 30 minutes to bring it to a static state. Sodium azide was added to the serum, until its concentration in the serum was brought to 0.05% for the purpose of antisepsis. To this antiserum, there were added one third (⅓) by volume of the serum of normal human and one third (⅓) by volume of the concentrated ascites from a patient suffering from cirrhosis of the liver (the amount of protein is 80 mg/ml) per 1 ml of the antiserum, and the mixture was incubated at 37° C. for one hour, then at 4° C. for 48 hours. Subsequently, it was centrifuged at 3,000 r.p.m. for 30 minutes at 4° C. to collect the supernatant. As the result of identification by the Ouchterlony method, using the concentrated original ascites as the antigen, and by the immunoelectrophoresis method, it was proved that the above-treated antiserum contained no antibody other than the NEA antibody.

EXAMPLE 5

Isolation and purification of the NEA by affinity chromatography

The NEA was isolated and purified by an affinity chromatography from a monospecific antibody of the NEA.

To 50 ml of the monospecific rabbit antiserum of the NEA prepared according to Example 3, an equivalent amount of 0.05% M phosphate physiological saline buffer solution at pH 7.5 was added. To said mixture, an equivalent amount of saturated ammonium sulphate solution of pH 7.8 was added. After 60 minutes, the solution was centrifuged at 5,000 r.p.m. and the resulting precipitates were dissolved in the same buffer solution as mentioned above, so as to form a solution having the same amount as that of the original antiserum. One fourth (¼) by volume of saturated ammonium sulphate solution at pH 7.8 was then added to said solution. After the subsequent 60 minutes, the solution was centrifuged at 5,000 r.p.m. Another one fourth (¼) by volume of the same saturated ammonium sulphate solution was added to the resulting supernatant, so that 33% ammonium sulphate solution is obtained. After 60 minutes, the solution was centrifuged at 5,000 r.p.m. to collect the γ-globulin fraction as precipitate. The precipitate was dissolved in about 15 ml of 0.01 M phosphate buffer solution at pH 8.0. The de-salting out and bufferization of said solution were carried out by fractionizing 15 ml of the solution by a gel filtration method employing a column of 2.6 cm in diameter and 40 cm in length filled with Sephadex G-50, and the same phosphate buffer solution, and collecting the protein fraction which was first eluted. This solution was concentrated and adjusted by using the protein bag, so that a concentration of protein amounted to 70 mg/ml. Activated DEAE-cellulose was filled in a column of 2.6 cm in diameter and 40 cm in length using said phosphate buffer solution. The above concentrated solution was added to said column, so that the solution may be absorbed by the column bed. The bed was filled with phosphate buffer solution, which was then continuously flowed through the column. Most of the immuno globulin G is not absorbed in the DEAE-cellulose, while all other proteins are absorbed. The eluate was divisionally collected, and the optical absorption at the wave length of 280 nm was determined, and the solution of the protein fraction was obtained. The immuno globulin G was thus isolated. Said fractional solution was further concentrated by using the protein bag, so that the concentration of protein amounted to 10 mg/ml. To 50 ml of bromocyanide-activated Sephalose 4B gel, there were added said immuno globulin G having the NEA antibody activity in an amount of 5 mg per 1 ml of the gel. The mixture was reacted at room temperature (20°–25° C.) for 6 hours, so as to fix the immuno globulin. Unreacted immuno globulin was removed by sufficient washing with the phosphate physiological saline buffer solution. Said Sephalose 4B gel was filled in a column of 2.6 cm in diameter and 20 cm in length using said phosphate physiological saline buffer solution. To 10 ml of physiological saline solution, there were dissolved 20 mg (amount of protein) of the partially purified NEA which was prepared according to Example 1. The resulting solution was added to said column to react with the NEA antibody fixed on the Sephalose 4B gel, and the NEA antigen antibody complex was thus prepared in the gel.

After washing the unreacted protein with said phosphate physiological saline buffer solution, 0.2 M sodium carbonate solution (pH 11.5) was added in the column to dissociate and dissolve out the NEA. The NEA solution collected was subjected to dialysis and concentrated. The concentrated solution was maintained at 4° C. The resulting NEA showed a single sedimentation line by the Ouchterlony method and the immunoelectrophoresis using the serum of normal human serum and the anti-NEA serum which is obtained before neutralizing with the colostrum-purified γ-globulin. Further, the isolated NEA showed a single band using 10% sodium dodecyl sulphite (SDS) polyacrylamide gel disc electrophoresis, showing that the NEA specimen had a high purity.

EXAMPLE 6

Purification of the NEA by means of basic anion exchange resin 500 ml of ascites of a patient suffering from primary cancer of the liver cells were concentrated to about 150 ml (concentration of protein is about 7%) in a 30% solution of polyethylene glycol (molecular weight about 15,000) dissolved in a phosphate buffer solution (pH 7.0 and ionic strength of 0.05). The concentrated solution was centrifuged under 5,000 G for 30 minutes. The supernatant solution was subjected to dialysis at 4° C. for three days in phosphate buffer solution of ionic strength of 0.05 at pH 7.0, by using cellulose tube for dialysis. Separately, QAE-Sephadex A-50 was previously wetted and equilibrated by the use of phosphate buffer solution of ionic strength of 0.05 at pH 7.0. The QAE-Sephadex A-50 was charged in the column (5 cm in diameter: 40 cm in length). Thereafter, 500 ml of the above sample for dialysis were added to the column. After the sample was absorbed on the column bed, the above phosphate buffer solution is filled in the upper portion of the bed, and continuously flowed therethrough. Almost no amount of the NEA or immuno globulin G was absorbed on the ion exchanger, and they flowed out of the column, while the other proteinous matters were absorbed. The solution which flowed out was fractionized, and the absorption band of 280 mµ was measured, so as to collect the fractional solution of protein, which showed a single precipitation line by means of Ouchterlony method, using antibody serum-protein rabbit antiserum. This was proved to be human immuno globulin G, by the same manner wherein anti-human immuno globulin G antibody is used.

Further, it was proved that the above fractional solution of protein involves the NEA, by means of Ouchterlony method using anti-NEA rabbit serum.

On the other hand, the concentrated solution of the fractional solution of protein was subjected to the identification test by electrophoresis using cellulose acetate membrane.

According to the result, the proteinous band was recognized in the γ-globulin region alone; whereas the proteinous bands were not recognized in the other globulin regions and albumin region. There were thus recovered about 5% NEA according to the above method, the purification degree amounting to about 6-times per protein ratio.

EXAMPLE 7

Purification of the NEA monospecific antibody by affinity chromatography

The partially purified NEA prepared according to Example 2 was dissolved in 0.05 M phosphate physiological saline buffer solution, so as to adjust the amount of protein to 10 mg/ml. This solution was added in an amount of double volume, to the Sephalose 4B gel which was activated by bromocyanide. The mixture was reacted at 4° C. for 24 hours to fix the protein of the partially purified NEA on the gel. Unreacted protein was removed by washing sufficiently with the same buffer solution. The gel was charged into a column of 1.5 cm in diameter and 20 cm in length. Into the column, there was added the solution of the purified rabbit immuno globulin G solution (protein concentration: 10 mg/ml) containing the NEA antibody which was obtained by purifying with an ion exchange chromatography after salting out ammonium sulphate according to Example 5. The solution was reacted with the NEA fixed to the Sephalose 4B gel, to prepare the NEA antigen-antibody complex in the gel. After the removal of unreacted immuno globulin G protein by washing sufficiently with phosphate physiological saline buffer solution, 0.2 M sodium carbonate solution (pH 11.5) was added to the column to dissociate the elute the NEA antibody. The NEA antibody fraction was collected, and neutalized by adding the fifth (1/5) by volume of 1 M glycine-hydrochloric acid buffer solution (pH 2.5). The resulting solution was subjected to Sephadex G-25 column chromatography, and eluted with 0.05 M phosphate physiological saline buffer solution to remove the glycine.

The resulting NEA exhibited a single precipitation line by the Ouchterlony method and the immunoelectrophoresis method using the anti-rabbit serum-protein serum of sheep, and also exhibited a single precipitation line with anti-rabbit γ-globulin serum of sheep, while the precipitation line did not appear in the Ouchterlony method and the immunoelectrophoresis, using anti-human serum protein serum and anti-colostrum protein serum. In view of these results, the NEA antibody is the rabbit immuno globulin G consisting of only the NEA antibody in high purity. This NEA antibody showed antibody value as high as about 100 times the original antiserum to the ratio of the amount of protein.

EXAMPLE 8

Process for the production of the NEA antibody from the isolated-purified NEA 100 µg of the purified NEA prepared according to Example 5 was dissolved in 0.5 ml of physiological saline solution. This solution was admixed with an equivalent amount of the Freund complete adjuvant, and the mixture was emulsified.

One milliliter of this emulsion was divisionally subjected to an intracutaneous injection, a subcutaneous injection, and an intramuscular injection in the hind leg and the belly of a rabbit having the weight of 2 Kg. In addition, immunization was effected twice in the same manner using the same amount of the antigen adjuvant emulsion every two weeks. The blood was collected 10 days from the last injection, and the serum was separated. The serum was then kept at 56° C. for 30 minutes to render it inactive. Sodium azide was added to the serum, so that the concentration amounted to 0.05% for the purpose of antisepsis. By the Ouchterlony method and immunoelectrophoresis method using an extract of the tissue of cancer of the breast as the antigen, it was proved that the resulting antiserum contains only the NEA antibody.

This impure antiserum was purified. More particularly, an equivalent amount of 0.05 M phosphate physiological saline buffer solution at pH 7.5 was added to 50 ml of the antiserum. To this solution, the same amount of the saturated ammonium sulphate solution at pH 7.8 was further added. After 60 minutes, the solution was centrifuged at 5,000 r.p.m. and the resulting precipitates were dissolved in the same phosphate physiological saline buffer solution, so that the amount of the solution was the same as that of the original antiserum. To said solution, one fourth (¼) by volume, on the basis of the solution, of the saturated ammonium sulphate was added. After allowing to stand for 60 minutes, said solution was centrifuged at 500 r.p.m. To the resulting supernatant, one fourth (¼) by volume, on the basis of said supernatant, of the saturated ammonium sulphate solution was further added to form 33% ammonium sulphate solution. After allowing to stand for 60 minutes, said solution was centrifuged at 5,000 r.p.m. and the precipitated γ-globulin fraction was collected. The precipitate was dissolved in about 15 ml of 0.01 M phosphate buffer solution of pH 8.0. This solution was subjected to de-salting out and bufferization to fractionize 15 ml of the solution by a gel filtration using a column of 2.6 cm in diameter and 40 cm in length which was filled with Sephadex G-50, and using the same phosphate buffer solution, to collect a protein fraction eluted first. The solution was then concentrated to the protein concentration of 70 mg/ml using the protein bag.

Activated DEAE-cellulose was then filled into a column of 2.6 cm in diameter and 40 cm in length with the same phosphate buffer solution. To this column, the concentrated solution was added, which was then sucked into the column bed, and the column was filled with the phosphate buffer solution, which was then continuously flowed over the bed.

Most of the immuno globulin G is not adsorbed on DEAE-cellulose, while all other proteins are absorbed. The eluate was then divisionally collected, and its optical absorption at the wave length of 280 mm was determined, to obtain the protein fraction.

The immuno globulin G containing the NEA antibody was thus isolated and collected.

This fractionated solution was concentrated by a protein bag and adjusted to a protein concentration of 10 mg/ml.

EXAMPLE 9

Process for the production of the NEA antibody using NEA-NEA antibody complex

One liter of ascites containing the NEA collected from a patient suffering from primary cancer of the liver cells was concentrated to about 300 ml using an ultrafiltration membrane (filterable molecular weight of 10,000), and centrifuged at 40,000 G for 30 minutes at 4° C. The supernatant was collected to use as the NEA antigen solution.

On the other hand, 50 ml of the NEA monospecific rabbit antiserum prepared according to Example 3 were centrifuged at 40,000 G for 30 minutes at 4° C., and the supernatant was collected to use as the NEA antibody solution.

All of the NEA antigen solution and the NEA antibody solution were admixed together, and incubated at 37° C. for one hour, and then at 4° C. for 24 hours. Subsequently, the mixed solution was centrifuged at 10,000 G for 20 minutes at 4° C., the supernatant was eliminated, and the NEA antigen-antibody complex was collected as a precipitate. To this precipitate, 50 ml of ice-cooled physiological saline solution were added to suspend the precipitate. The suspension was centrifuged at 10,000 G for 20 minutes at 4° C. The supernatant was eliminated, and the precipitate was again obtained. To the precipitate, the same amount of the ice-cooled physiological saline solution was added, and the same procedures were repeated twice to obtain a precipitate. To this NEA antigen-antibody complex, 20 ml of 0.1 M glycine-hydrochloric acid buffer solution at pH 1.8 were added to dissociate the complex for 30 minutes at the temperature of 4° C. This solution was then centrifuged at 30,000 G for 20 minutes at 4° C. and the supernatant was collected. To this supernatant, 0.4 M disodium hydrogen phosphate solution was added to neutralize the supernatant and to adjust the pH value to 7.0. The NEA antigen-antibody complex was again produced by such neutralization. Further, the operation ranging from the step of mixing the NEA antigen solution with the NEA antibody solution, to the step of neutralization, was repeated twice. The finally neutralized solution was incubated at 37° C. for one hour, then at 4° C. for 24 hours, and subsequently centrifuged at 10,000 G for 20 minutes at 4° C. The supernatant was eliminated, to obtain the NEA antigen-antibody complex. This complex was suspended in physiological saline solution and the concentration of protein was adjusted to 2 mg/ml. An emulsion was prepared by admixing 0.5 ml of this solution with 0.5 ml of the Freund complete adjuvant. This emulsion was subjected to an intracutaneous injection, a subcutaneous injection, and an intramuscular injection in the hind leg and the belly of a rabbit having a weight of 2 Kg. After two weeks, additional immunization was effected by another one milliliter of the NEA antigen-antibody complex prepared according to the same procedure as described above. After a subsequent two weeks, the immunization was repeated again with an additional one milliliter of the same emulsion. The blood was collected 10 days from the last immunization, and the serum was separated. The serum was incubated at 56° C. for 30 minutes to render it inactive, and sodium azide was added thereto to result in a concentration of 0.05% for the purpose of antisepsis. As the result of identification by the Ouchterlony method and the immunoelectrophoresis method wherein there is employed as an antibody the concentrated solution of the original ascites used for the preparation of the NEA antigen-antibody complex, it was proved that this antserum does not contain antibodies other than the NEA antibody.

EXAMPLE 10

Detection of the NEA in serum of patient by the Ouchterlony method

The NEA in the serum of patients suffering from various kinds of diseases was detected by the Ouchterlony method.

A plate of 1.2% agarose was made from 0.05 M phosphate physiological saline buffer solution at pH 7.5 (containing 0.05% sodium nitride). The plate was 1.2 mm in thickness. The size of the antigen well (that is, the well in which the test serum is placed) and also the antibody well was 4 mm in diameter, and the distance between the centers of the two wells was 7 mm. The detection of the NEA was effected by injecting 10 μl of the anti-NEA rabbit serum prepared according to Example 8 into the antibody well, and injecting 40 μl of the test serum into the antigen well.

The identification of the NEA was effected by using, as the authentic substance for a standard, the NEA of high purity which was prepared according to Example 5. More particularly, such identification was carried out by examining two precipitation lines as to whether or not they are perfectly fused, i.e. coincide with each other, wherein one of the two precipitation lines occurs by the reaction between the authenic NEA and the anti-NEA rabbit serum, and the other precipitation line occurs by the reaction between the test serum and the anti-NEA rabbit serum. It was thus confirmed that the latter precipitation line is due to the NEA. Results are shown in the following Table 1.

Table 1

| Test Serum | | Number of specimens | Number of positive data | Number of negative data |
|---|---|---|---|---|
| Serum of neoplasm patient | Cancer of the stomach | 25 | 8 | 17 |
| | Cancers of the colon and of the rectum | 12 | 2 | 10 |
| | Cancer of the pancreas | 8 | 2 | 6 |
| | Primary cancer of the liver | 12 | 4 | 8 |
| | Uterine cancer and ovarian cancer | 10 | 3 | 7 |
| | Cancer of the breast | 9 | 5 | 4 |
| | Leukemia | 6 | 2 | 4 |
| | Lymphosarcoma | 2 | 1 | 1 |
| Serum of non-neoplasm patient | Normal human | 31 | 0 | 31 |
| | Gastritis, Gastric ulcer, Duodenal ulcer | 32 | 0 | 32 |
| | Colitis | 6 | 0 | 6 |
| | Hepatitis and Cirrhosis of the liver | 18 | 0 | 18 |
| | Mastitis | 3 | 0 | 3 |
| | Chronic pancreatitis | 3 | 0 | 3 |
| | Pancreatitis | 3 | 0 | 3 |
| | Rheumatic fever | 3 | 0 | 3 |
| | Chronic articular rheumatism | 5 | 0 | 5 |
| | Other benign diseases | 7 | 0 | 7 |

As can be seen from the above Table 1, the NEA was detected in 27 among a total of 84 samples of the serum collected from the neoplasm patients, the percentage of detection being 32.1%. On the other hand, NEA could not be detected among a total of 111 samples of the serum collected from the non-neoplasm patients, including the serum of normal humans. It was thus shown that the NEA has high monospecificity to the neoplasm, and the detection test of the serum NEA using the NEA antibody can be used for the diagnosis of neoplasm.

EXAMPLE 11

Detection of the NEA in the serum of patient by a single radial immunodiffusion method The NEA in serum of patients suffering from various kinds of diseases was detected by the single radial immunodiffusion method.

In view of the consideration that the amount of the NEA in the serum of malignant neoplasm patients varies over a comparatively wide range, an attempt was made to improve the detection of the NEA by preparing two plates having different concentrations of the antibody, and inspecting the original serum simultaneously on the two plates, for the purpose of preventing the impossibility of detection owing to an excess or shortage of the antibody.

In the case of the plate of low concentration of the antibody, it is difficult to macroscopically observe the precipitation ring which is formed by the antigen-antibody complex, because the precipitation is very faint. For this reason, the detection was achieved in the following manner.

After the antigen was reacted sufficiently with the antibody, the plate was dipped into the buffer solution to dissolve unreacted antibody in the buffer solution from the agar.

On the other hand, an antiserum was prepared, using a serum immuno globulin of the same animal as was used for the preparation of said antibody, and immunizing the other kind of animal with said globulin.

This antiserum was injected into each antigen well, and incubated for a definite period of time.

When the NEA antigen-antibody exists, there can be macroscopically observed the precipitation ring which is the reaction product between the NEA antigen-antibody with the antibody which was subsequently added. That is to say, this method is called "a single radial immunodiffusion method employing a two-antibody process."

(1) Preparation of single radial immunodiffusion plate

Agarose is dissolved under heat to obtain a concentration of 1.2% in 0.1 M tris-hydrochloric acid physiological saline buffer solution of pH 8.0 which includes 0.1% of sodium azide for antisepsis, so that gelation occurs. The temperature of the agarose gel was brought to about 50° C. The anti-NEA rabbit serum prepared according to Example 3 was heated to about 50° C. and was then admixed with said gel in order to prepare two mixtures, one of which contains 2% of antiserum for the high concentration plate, and the other of which contains 0.4% of antiserum for the low concentration plate. The mixtures were poured onto a glass plate, or into a plastic pan or vat, to make a plate (1.2 mm thick) of agarose gel containing the anti-NEA serum. Antigen wells of 4 mm in diameter were bored to an equal and sufficient depth in said plate.

(2) Detection of the NEA antigen in the test serum by a single radial immunodiffusion method 10 μl of the test serum was injected simultaneously into each of the antigen wells in both plates, one for high concentration of the antibody, and one for low concentration of the antibody, respectively. After all the serums were absorbed in the gel, the plates were allowed to stand for 48 hours in a wetting box at room temperature. An observation was made to determine the existence of a precipitation ring for the plate of high concentration, showing whether or not NEA is present.

On the other hand, the plate of low concentration of the antibody was dipped for three days in the same buffer solution that was used for the preparation of the gel plate, to eliminate the unreacted NEA antibody in the gel. The buffer solutions were renewed twice every day, i.e. morning and evening. The gel plate was taken out of the buffer solution, and the buffer solutions in the antigen walls were removed. 10 μl of the anti-rabbit immuno globulin goat serum was injected into each of the antigen wells, respectively. After all the antiserums were abosrbed in the gel, the plate was allowed to stand for 24 hours in a wetting box at room temperature. The presence of the NEA was determined as above, by observing whether or not a precipitation ring was formed. The data are shown in the following Table 2.

Table 2

| Test Serum | | Number of specimens | Number of positive data | Number of negatove data |
|---|---|---|---|---|
| Serum of neoplasm patient | Cancer of the stomach | 27 | 10 | 17 |
| | Cancers of the colon and of the rectum | 14 | 3 | 11 |
| | Cancer of the pancreas | 8 | 2 | 6 |
| | Primary cancer of the liver | 19 | 9 | 10 |
| | Uterine cancer and ovarian cancer | 10 | 3 | 7 |
| | Cancer of the breast | 12 | 8 | 4 |
| | Leukemia | 6 | 2 | 4 |
| | Lymphosarcoma | 2 | 1 | 1 |
| Serum of | Normal human | 31 | 0 | 31 |

Table 2-continued

| Test Serum | | Number of specimens | Number of positive data | Number of negative data |
|---|---|---|---|---|
| non-neoplasm patient | Gastritis, Gastric ulcer, Duodenal ulcer | 32 | 0 | 32 |
| | Colitis | 6 | 0 | 6 |
| | Hepatitis and Cirrhosis of the liver | 45 | 1 | 44 |
| | Mastitis | 3 | 0 | 3 |
| | Chronic pancreatitis | 3 | 0 | 3 |
| | Pancreatitis | 4 | 0 | 4 |
| | Rheumatic fever | 5 | 0 | 5 |
| | Chronic articular rheumatism | 5 | 0 | 5 |
| | Other benign diseases | 7 | 0 | 7 |

As can be seen from Table 2, the NEA was detected in 38 among a total of 98 samples of the serum collected from the neoplasm patients, the percentage of detection being 38.8%. On the other hand, the NEA was not detected in 140 among the total of 141 samples of serum from non-neoplasm patients, including the serum of normal humans. The single exception involved a patient who was clinically diagnosed as suffering from cirrhosis of the liver, thus involving a possible complication with primary cancer of the liver cells.

From the above results, it is obvious that the detection of the NEA in serum according to the method of this invention is also very advantageous for the diagnosis of malignant neoplasm.

EXAMPLE 12

Diagnosis reagent for neoplasm by immunological detection method based on an agglutination reaction (PHA method, RPHA method)

(a) NEA antibody sensitized erythrocytes of sheep

The blood of sheep preserved in Alserver solution was centrifuged at 2,000 r.p.m. for 10 minutes at 4° C. to eliminate the plasma, washed 5 times with physiological saline solution, and then again centrifuged at 2,000 r.p.m. for 10 minutes. This sheep erythrocytes was made into a 5% suspension by adding the phosphate physiological saline buffer solution. To this suspension, there was added dropwise and slowly, by means of a dropping funnel, one fifth (1/5) by volume, on the basis of the suspension, of 2.5% glutaraldehyde diluted with ice-cooled phosphate physiological saline buffer solution. The suspension was stirred for 5 hours at room temperature, washed 5 times with physiological saline solution, and then settled by centrifuging at 2,000 r.p.m. for 5 minutes. An ice-cooled phosphate physiological saline buffer solution containing thimerosal was added to the precipitate, so as to obtain a 5% glutaraldehyde-treated sheep erythrocytes suspension. To this erythrocyte solution, an equivalent amount of 0.0025% tannic acid solution was added, and the mixture was centrifuged for 15 minutes. The supernatant was eliminated. The precipitate was washed 5 times with physiological saline solution, and then centrifuged again. To the resulting precipitate, phosphate physiological saline buffer solution was added. 5% glutaraldehyde-tannic acid treated erythrocytes of sheep was thus produced.

To this erythrocytes, an equivalent amount (10 µg/ml) of the NEA antibody prepared according to Example 7 was added. The whole was stirred for 30 minutes at room temperature, and then centrifuged. The resulting precipitate was washed twice with physiological saline solution, and diluted with the phosphate physiological saline buffer solution. 10% glutaraldehyde-tannic acid treated NEA antibody sensitized sheep erythrocytes suspension was thus produced.

The sensitivity of detection for the NEA was 150 ng/ml by RPHA method using the NEA antibody sensitized erythrocytes of sheep. Thus, a very small amount of the NEA can be detected in the test serum.

(b) NEA sensitized erythrocytes of sheep

To 5% glutaraldehyde-tannic acid treated erythrocytes of sheep prepared according to (a) above, an equivalent amount (10 µg/ml) of the NEA prepared according to Example 5 was added. The mixture was stirred for 30 minutes at room temperature, and centrifuged at 2,000 r.p.m. for 10 minutes. The precipitate was washed twice with physiological saline solution, and diluted with the phosphate physiological saline buffer solution, to produce a 10% glutaraldehyde-tannic acid treated NEA sensitized sheep erythrocytes suspension.

The sensitivity of detection for the NEA was 200 ng/ml, by the PHA method using said NEA sensitized erythrocytes of sheep.

EXAMPLE 13

Detection of NEA in the serum of the patient by an immunoelectro-osmophoresis using a carbamylated NEA antibody (a) Carbamylation of the NEA antibody The anti-NEA rabbit immuno globulin antibody prepared according to Example 8 was adjusted, so that the protein concentration amounted to 7 mg/ml. To 10 ml of this solution, 70 ml of boric acid buffer solution at pH 8.0 (the buffer solution was previously prepared by dissolving 9.03 g of $H_3BO_3$, 2.13 g of NaCl and 5.18 g of $Na_2B_4O_7.10 H_2O$ in water to a total volume of one liter) and 20 ml of 1.0 M potassium cyanate were added, followed by incubating at 45° C. for 120 minutes. This solution was cooled to 4° C. to terminate the reaction. The resulting solution was concentrated to about 10 ml, by putting it in a cellulose tube for dialysis, and placing the tube in a 30% polyethylene glycol (molecular weight of about 15,000) solution of 0.05 M phosphate buffer solution at pH 7.5. About 10 ml of the concentrated solution was subjected to de-salting and buffering by means of column chromatography, using a column of 2.6 cm in diameter and 40 cm in length filled with Sephadex G-25 which was previously swelled and equilibrated by 0.05 M phosphate buffer solution at pH 7.5. The resulting antibody was then concentrated to a protein concentration of about 70 mg/ml by means of a protein bag.

The resulting carbamylated NEA antibody solution was subjected to immunoelectrophoresis in agar gel, and the NEA was injected into a conventional longitudinal basin. A precipitation line appeared at the $\alpha_2$-globulin region. In the case of the NEA antibody solution prior to the carbamylation, as the control, the precipitation line appeared at the $\gamma$-globulin region.

As the result, it was found that carbamylation of the NEA antibody changed its electromobility, so that the precipitation line was shifted to the anode side, although the antibody still maintained its activity even after carbamylation.

(d) Detection of the NEA in the test serum

The detection of the NEA in the test serum was effected by the following steps:

1.2% agar plate of 1.2 mm in thickness was prepared from Veronal buffer solution at pH 8.6 having ionic strength of 0.025;

A pair of wells 4 mm in diameter with a distance of 7 mm therebetween were made in the plate;

10 μl of the test serum were injected into the well located at the anode side, whereas 10 μl of the carbamylated NEA antibody solution according to (a) above were injected into the other well located at the cathode side;

Electrophoresis was effected for 40 minutes by an electric current through the plate at 2.5 mA per cm of width of the plate; and Observation was made as to whether a precipitation line exists.

The results are shown in the following Table 3.

Table 3

|  | Test Serum | Number of specimens | Number of positive data | Number of negative data |
|---|---|---|---|---|
| Serum of neoplasm patient | Cancer of the stomach | 25 | 8 | 17 |
|  | Cancer of the colon and of the rectum | 12 | 2 | 10 |
|  | Cancer of the pancreas | 8 | 2 | 6 |
|  | Primary cancer of the liver | 19 | 8 | 11 |
|  | Uterine cancer and ovarian cancer | 10 | 3 | 7 |
|  | Cancer of the breast | 12 | 7 | 5 |
|  | Leukemia | 6 | 2 | 4 |
|  | Lymphosarcoma | 2 | 1 | 1 |
| Serum of non-neoplasm patient | Normal human | 31 | 0 | 31 |
|  | Gastritis, Gastric ulcer, Duodenal ulcer | 32 | 0 | 32 |
|  | Colitis | 6 | 0 | 6 |
|  | Hepatitis and Cirrhosis of the liver | 41 | 1 | 40 |
|  | Mastitis | 3 | 0 | 3 |
|  | Chronic pancreatitis | 3 | 0 | 3 |
|  | Pancreatitis | 3 | 0 | 3 |
|  | Rheumatic fever | 5 | 0 | 5 |
|  | Chronic articular rheumatism | 5 | 0 | 5 |
|  | Other benign diseases | 7 | 0 | 7 |

As can be seen from Table 3, the NEA was detected in 33 among a total of 94 samples of the serum collected from the neoplasm patients, the percentage of detection being 35.1%. On the other hand, the NEA was not detected in 135 among a total of 136 samples of the serum from non-neoplasm patients, including the serum of normal humans. The single exception involved a patient who was clinically diagnosed as suffering from cirrhosis of the liver, thus possibly involving a complication with primary cancer of the liver cells.

From the above results, it can be seen that the detection of the NEA in the serum using the reagent according to this invention is very advantageous for the diagnosis of malignant neoplasm.

EXAMPLE 14

Detection of the NEA in the serum of patient by radio immuno assay (RIA)

(a) Labelling of the NEA by Chloramine T process

Labelling was effected with respect to the NEA which was prepared according to Example 5. The following solutions were mixed.

| | |
|---|---|
| NEA solution (1.25 mg/ml) | 20 μl |
| $^{125}$I-Na (0.1 millicurie/μl) | 10 μl |
| 0.4 M phosphate buffer solution (pH 7.4) | 50 μl |

To the mixture, there were added 50 μl of Chloramine T (1.2 mg/ml), and the whole was stirred for 30 seconds. 50 μl of sodium metabisulfite solution (3.0 mg/ml) were added to the mixture, and the whole was stirred for two minutes. 100 μl of non-radioactive potassium iodide solution (10 mg/ml) were added to the mixture. This solution was subjected to column chromatography by means of Sephadex G-75, and eluted with 0.05 M phosphate physiological saline solution (pH 7.4). The eluate was divisionally collected into test tubes which were previously filled with one milliliter of 0.05 M phosphate physiological saline buffer solution—1% bovine serum albumin.

When the labelled NEA fraction was recovered, $^{125}$I-NEA having specific radioactivity of 10 millicurie/mg was obtained. This $^{125}$I-NEA can be used as a diagnosis reagent for neoplasm.

(b) Detection of the NEA by the double antibody process using $^{125}$I-NEA

At first, a standard curve was drawn up using a standard NEA material wherein the content of the NEA was known, and $^{125}$I-NEA prepared according to (a) above. More particularly, the reaction mixture was made by mixing 0.1 ml of the standard NEA material, 0.1 ml of $^{125}$I-NEA (10,000 cpm) prepared according to (a), and 0.5 ml of 0.05 M phosphate physiological saline buffer solution—1% bovine serum albumin solution. To this reaction mixture, there was added 0.1 ml of the solution which was previously prepared by diluting 20,000-40,000—fold the anti-NEA rabbit serum prepared according to Example 3. The mixture was reacted at 4° C. for 24 hours. To the reaction mixture, there were added 0.1 ml of the normal rabbit serum solution which was diluted 100-fold, and 0.1 ml of anti-rabbit γ-globulin goat serum solution which was diluted 10-fold as a second antibody, and the whole was reacted at 4° C. for 24 hours. This solution was placed in a test tube and centrifuged at 3,000 r.p.m. for 30 minutes, followed by removing the supernatant. The radioactivity of the precipitate in the test tube was measured.

A very accurate standard curve was thus obtained in the NEA concentration range of 5-320 ng/ml, as the result of the RIA method according to the process as described above.

The RIA method was effected in the same manner as that described above, with respect to a total of 381 samples of serum, consisting of 55 samples from normal humans, 129 samples from non-neoplasm patients, and 197 samples from neoplasm patients. The results are shown in the following Table 4.

Table 4

|  | Case | Total number of cases | NEA conc. of over 200ng/ml number of cases | NEA conc. of over 200ng/ml Percentage (%) |
| --- | --- | --- | --- | --- |
| Serum of neoplasm patient | Cancer of the stomach | 68 | 21 | 30.9 |
|  | Cancer of the large intestine | 29 | 10 | 34.5 |
|  | Cancer of the pancreas | 10 | 6 | 60.0 |
|  | Cancer of the liver | 21 | 9 | 42.9 |
|  | Cancers of the gall-bladder and the bile duct | 10 | 3 | 30.0 |
|  | Cancer of the lung | 3 | 1 | 33.3 |
|  | Cancer of the breast | 17 | 7 | 41.2 |
|  | Uterine cancer and ovarian cancer | 11 | 3 | 27.3 |
|  | Leukemia | 24 | 12 | 50.0 |
|  | Other malignant tumors | 4 | 2 | 50.0 |
|  | Total | 197 | 74 | 37.6* |
| Serum of normal human and non-neoplasm patient | Normal human | 55 | 0 | 0 |
|  | Acute hepatitis | 6 | 1 | 16.7 |
|  | Chronic hepatitis | 23 | 4 | 17.4 |
|  | Cirrhosis of the liver | 21 | 1 | 4.8 |
|  | Other benign diseases | 79 | 3 | 3.8 |
|  | total | 184 | 9 | 4.9** |

*Average * $\frac{74}{197} \times 100 = 37.6\%$

**Average * $\frac{9}{184} \times 100 = 4.9\%$

As can be seen from Table 4, the determination of NEA in the serum by the RIA method is useful for the diagnosis of neoplasm.

(c) Labelling of the NEA antibody by Chloramine T process

Labelling was effected with respect to the NEA antibody which was prepared according to Example 7. The following solutions were mixed.

| | |
| --- | --- |
| NEA antibody solution (1.0 mg/ml) | 20 μl |
| $^{125}$I-Na(0.1 millicurie/μl) | 10 μl |
| 0.4 M phosphate buffer solution (pH 7.4) | 50 μl |

To the mixture, there were added 100 μl of chloramine T (1.0 mg/ml), and the whole was stirred for one minute. 100 μl of sodium metabisulphite (2.4 mg/ml) were added to the mixture which was in turn stirred for two minutes. 100 μl of non-radioactive potassium iodide (10 mg/ml) were added to the mixture. This reaction solution was subjected to column chromatography using Sephadex G-75, and eluted with 0.05 M phosphate physiological saline buffer solution (pH 7.4). This eluate was collected divisionally into test tubes which were previously filled with one milliliter of 0.05 M phosphate physiological saline buffer solution—1% bovine serum albumin solution. When the fraction of labelled NEA antibody was recovered, $^{125}$I-NEA antibody having a specific radioactivity of 10 millicurie/mg was obtained. The $^{125}$I-NEA antibody is used as a diagnosis reagent for neoplasm.

What is claimed is:

1. Substantially pure neoplasm embryonic antigen, characterized by a molecular weight of about 100,000±20,000, a photo-absorption coefficient of $E_1^{0.1\%}$ $cm$ 280=0.936, an isoelectric point of pH 9.1–9.4, and movement in the γ-globulin region by immunoelectrophoresis.

2. Diagnosis reagent for neoplasm, comprising an antibody of the neoplasm embryonic antigen of claim 1.

3. Diagnosis reagent for neoplasm comprising a gel plate which is prepared by dissolving an antibody of the neoplasm embryonic antigen of claim 1 in a hot solution of supporting medium selected from agar, agarose, starch, and polyacrylamide, and cooling the resulting solution to form a solid plate.

4. Diagnosis reagent for neoplasm as claim in claim 3, wherein the supporting medium is agarose.

5. Diagnosis reagent for neoplasm, comprising an antibody of the neoplasm embryonic antigen of claim 1, which antibody has been carbamylated.

6. Diagnosis reagent for neoplasm, comprising the neoplasm embryonic antigen of claim 1 labelled with a radioactive isotope or neoplasm embryonic antigen antibody labelled with a radioactive isotope.

7. Diagnosis reagent for neoplasm as claimed in claim 6, wherein the radioactive isotope is $^{125}$I.

8. Diagnosis reagent for neoplasm, comprising the neoplasm embryonic antigen of claim 1, bound to a particulate substance or neoplasm embryonic antigen antibody bound to a particulate substance.

9. Diagnosis reagent for neoplasm as claimed in claim 8, wherein the particulate substance is selected from the group consisting of blood cells of mammals and birds, polystyrene latex, polyester latex, vinyl chloride, bentonite, and glass beads.

10. Diagnosis reagent for neoplasm as claimed in claim 8, wherein the particulate substance is erythrocytes of sheep.

11. Diagnosis reagent for neoplasm as claimed in claim 8, wherein the particulate substance is blood cells of mammals or birds.

12. Diagnosis reagent for neoplasm as claimed in claim 8, comprising a product which is prepared by coating glutaraldehyde-tannic acid treated blood cells of mammals or birds with the neoplasm embryonic antigen or neoplasm embryonic antigen antibody.

13. Diagnosis reagent for neoplasm as claimed in claim 12, wherein the blood cells are erythrocytes of sheep.

14. Method for the diagnosis of human neoplasm by detecting the neoplasm embryonic antigen of claim 1, which comprises
  (a) mixing an antibody of the neoplasm embryonic antigen of claim 1, the neoplasm embryonic antigen of claim 1 labelled with a radioactive isotope, and test serum from the human,
  (b) separating the radioactive neoplasm embryonic antigen bound to the neoplasm embryonic antigen antibody from the radioactive neoplasm embryonic antigen in the reaction mixture, and
  (c) measuring the radioactivity of either of said separate fractions.

15. The method of claim 14, wherein the radioactive isotope in step (a) is $^{125}I$.

16. The method of claim 14, wherein the separation in step (b) is carried out by adding to the reaction mixture a second antibody which is able to bind to an neoplasm embryonic antigen-neoplasm embryonic antigen antibody complex, and collecting the resulting precipitate.

17. The method of claim 16, wherein the second antibody is anti-rabbit γ-globulin goat serum.

18. Method for the diagnosis of human neoplasm by detecting the neoplasm embryonic antigen of claim 1, which comprises mixing test serum from the human with an antibody of the neoplasm embryonic antigen of claim 1 bound to a particulate substance, and observing whether agglutination occurs in the mixture.

19. The method of claim 18, wherein the particulate substance is blood cells of mammals or birds.

20. The method of claim 18, wherein the particulate substance is sheep erythrocytes.

21. Method for the diagnosis of human neoplasm by detecting the neoplasm embryonic antigen of claim 1, which comprises injecting test serum from the human into a well in a gel plate of 1–2 mm in thickness containing an antibody of the neoplasm embryonic antigen of claim 1, and observing whether a precipation ring is formed on the plate.

22. The method of claim 21, wherein the gel plate is an agarose gel plate.

23. Method for the diagnosis of human neoplasm by detecting the neoplasm embryonic antigen of claim 1, which comprises
  (a) making a pair of wells in an agar plate of 1–2 mm in thickness,
  (b) injecting a carbamylated antibody of the neoplasm embryonic antigen of claim 1 into the well on the cathode side of the plate and injecting test serum from the human into the well on the anode side of the plate,
  (c) transmitting an electric current to the agar plate, and
  (d) observing whether a precipitation line is formed on the plate.

24. Process for the production of an antibody of the neoplasm embryonic antigen of claim 1, which comprises immunizing animals other than humans with the neoplasm embryonic antigen, and recovering antiserum containing the antibody from the immunized animals.

25. The process of claim 24, wherein the animal is a rabbit.

26. The process of claim 24, wherein the immunization is carried out with an emulsion of the neoplasm embryonic antigen and Freund complete adjuvant.

27. Method for obtaining the neoplasm embryonic antigen of claim 1, characterized by subjecting a material containing the neoplasm embryonic antigen of claim 1 to chromatography on a supporting material bound to an neoplasm embryonic antigen antibody to form an neoplasm embryonic antigen-neoplasm embryonic antigen antibody complex on the supporting material, and dissociating the complex to recover the neoplasm embryonic antigen.

28. Method for obtaining an antibody of the neoplasm embryonic antigen of claim 1, characterized by subjecting a material containing neoplasm embryonic antigen antibody to chromatography on a supporting material bound to neoplasm embryonic antigen to form an neoplasm embryonic antigen-neoplasm embryonic antigen antibody complex on the supporting material, and dissociating the complex to recover the neoplasm embryonic antigen antibody.

29. Purification method for obtaining the neoplasm embryonic antigen of claim 1, characterized by subjecting a material containing the neoplasm embryonic antigen of claim 1 to chromatography on a basic anion exchange resin, thereby absorbing impurities on the resin, and recovering the eluate containing the neoplasm embryonic antigen of claim 1.

* * * * *